United States Patent
Hayashi et al.

(10) Patent No.: US 10,758,199 B2
(45) Date of Patent: Sep. 1, 2020

(54) X-RAY DIAGNOSTIC APPARATUS AND IMAGE PROCESSING APPARATUS

(71) Applicant: Toshiba Medical Systems Corporation, Otawara-shi (JP)

(72) Inventors: Yoshiyasu Hayashi, Nasushiobara (JP); Nobuo Kobayashi, Nasushiobara (JP); Kunio Shiraishi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1010 days.

(21) Appl. No.: 14/837,545

(22) Filed: Aug. 27, 2015

(65) Prior Publication Data
US 2016/0022239 A1  Jan. 28, 2016

Related U.S. Application Data

(63) Continuation of application No. PCT/JP2014/054967, filed on Feb. 27, 2014.

(30) Foreign Application Priority Data

Feb. 27, 2013  (JP) .................................. 2013-037985

(51) Int. Cl.
*A61B 6/00* (2006.01)
*G06T 7/00* (2017.01)
(Continued)

(52) U.S. Cl.
CPC .............. *A61B 6/5217* (2013.01); *A61B 6/12* (2013.01); *A61B 6/40* (2013.01); *A61B 6/42* (2013.01);
(Continued)

(58) Field of Classification Search
CPC .......... A61B 6/00; A61F 2250/00; A61F 2/00; A61F 2/82; A61F 2/07; A61F 2250/0098;
(Continued)

(56) References Cited

U.S. PATENT DOCUMENTS 4,436,095 A * 3/1984 Kruger .................. A61B 6/481
                                                    348/E5.086
5,233,989 A * 8/1993 Honda ..................... G06T 5/50
                                                    600/425
(Continued)

FOREIGN PATENT DOCUMENTS

JP      2002-95640 A      4/2002
JP      2002095640 A  *   4/2002
(Continued)

OTHER PUBLICATIONS

Machine Translation of JP 2002095640 A.*
(Continued)

*Primary Examiner* — Pascal M Bui Pho
*Assistant Examiner* — Sean D Mattson
(74) *Attorney, Agent, or Firm* — Oblon, McClelland, Maier & Neustadt, L.L.P.

(57) ABSTRACT

In an X-ray diagnostic apparatus according to an embodiment, an X-ray generator configured to irradiate an X-ray to a subject. An X-ray detector configured to detect the X-ray. Processing circuitry configured to generate a plurality of X-ray images chronologically based on X-rays that have passed through the subject to which a contrast media is injected, and that have been detected by the X-ray detector. The processing circuitry configured to extract a first image from among the X-ray images, the first image when any one of a change in a pixel value between predetermined two images and a predetermined region in one image is equal to or smaller than a threshold. A display configured to display, after the first image is extracted, a plurality of X-ray images that have been generated prior to the first image in reverse chronological order.

9 Claims, 7 Drawing Sheets

(51) Int. Cl.
  *A61B 6/12* (2006.01)
  *A61F 2/82* (2013.01)
  *A61M 5/00* (2006.01)
  *A61F 2/07* (2013.01)

(52) U.S. Cl.
  CPC .............. *A61B 6/463* (2013.01); *A61B 6/481* (2013.01); *A61B 6/486* (2013.01); *A61B 6/504* (2013.01); *A61B 6/5235* (2013.01); *A61F 2/82* (2013.01); *A61M 5/007* (2013.01); *G06T 7/0016* (2013.01); *A61B 6/5205* (2013.01); *A61F 2/07* (2013.01); *A61F 2250/0098* (2013.01)

(58) Field of Classification Search
  CPC ........... A61M 5/00; A61M 5/007; G06T 7/00; G06T 7/0016; G01R 33/00
  See application file for complete search history.

(56) References Cited

U.S. PATENT DOCUMENTS

| | | | | |
|---|---|---|---|---|
| 7,505,551 | B2 * | 3/2009 | Grass | A61B 6/466 378/8 |
| 2002/0103437 | A1 | 8/2002 | Jibiki | |
| 2003/0004562 | A1 | 1/2003 | DiCarlo | |
| 2003/0088177 | A1 * | 5/2003 | Totterman | G06T 7/20 600/414 |
| 2003/0108149 | A1 * | 6/2003 | Tsuyuki | A61B 6/032 378/54 |
| 2004/0171932 | A1 * | 9/2004 | Raman | A61B 5/02007 600/425 |
| 2008/0031405 | A1 | 2/2008 | Matsumoto | |
| 2008/0137934 | A1 * | 6/2008 | Sakaguchi | A61B 6/4441 382/132 |
| 2009/0028409 | A1 | 1/2009 | Tsukagoshi et al. | |
| 2010/0104167 | A1 * | 4/2010 | Sakaguchi | A61B 6/12 382/132 |

FOREIGN PATENT DOCUMENTS

| | | |
|---|---|---|
| JP | 2002-238901 A | 8/2002 |
| JP | 2006-230484 A | 9/2006 |
| JP | 2007-44262 A | 2/2007 |
| JP | 2008-35895 A | 2/2008 |
| JP | 2009-45445 A | 3/2009 |
| JP | 2009-165846 A | 7/2009 |
| JP | 2010-284301 A | 12/2010 |
| JP | 2012-24404 A | 2/2012 |

OTHER PUBLICATIONS

International Search Report and Written Opinion dated Apr. 8, 2014 in PCT/JP2014/054967 filed Feb. 27, 2014 (with English translation).

* cited by examiner

X-RAY DIAGNOSTIC APPARATUS AND IMAGE PROCESSING APPARATUS

CROSS-REFERENCE TO RELATED APPLICATIONS

This application is a continuation of PCT international application Ser. No. PCT/JP2014/054967 filed on Feb. 27, 2014 which designates the United States, incorporated herein by reference.

FIELD

Embodiments described herein relate generally to an X-ray diagnostic apparatus and an image processing apparatus.

BACKGROUND

Conventionally, with X-ray diagnostic apparatuses, radiographic imaging is performed, injecting a contrast media into blood vessels of a patient, and by reading X-ray images of the imaged blood vessels to perform diagnosis and treatment. For example, in a cardiovascular examination by an X-ray diagnostic apparatus, while referring to an image of a blood vessel that has been given a contrast by injecting a contrast media into the blood vessel, a guide wire or a catheter is inserted forward.

In cardiovascular examinations, to further emphasize a contrast by a contrast media, image processing using multiple frames that correspond to a several-seconds period in which a flow of the contrast media is observed. For example, image processing to generate one piece of an image in which respective values of an identical pixel in multiple frames are signal averaged, image processing in which the largest value or the smallest value is selected among respective values of an identical pixel in multiple frames to generate one piece of image, and the like are performed. However, in the conventional technique described above, there is a case in which determination whether a residual contrast media is present is difficult.

DETAILED DESCRIPTION

According to an embodiment, an X-ray diagnostic apparatus includes an X-ray generator, an X-ray detector, processing circuitry and a display. The X-ray generator configured to irradiate an X-ray to a subject. The X-ray detector is configured to detect the X-ray. The processing circuitry is configured to generate a plurality of X-ray images chronologically based on X-rays that have passed through the subject to which a contrast media is injected, and that have been detected by the X-ray detector. The processing circuitry is configured to extract a first image from among the X-ray images, the first image when any one of a change in a pixel value between predetermined two images and a predetermined region in one image is equal to or smaller than a threshold. The display is configured to display, after the first image is extracted, a plurality of X-ray images that have been generated prior to the first image in reverse chronological order.

First Embodiment

Figure 1:
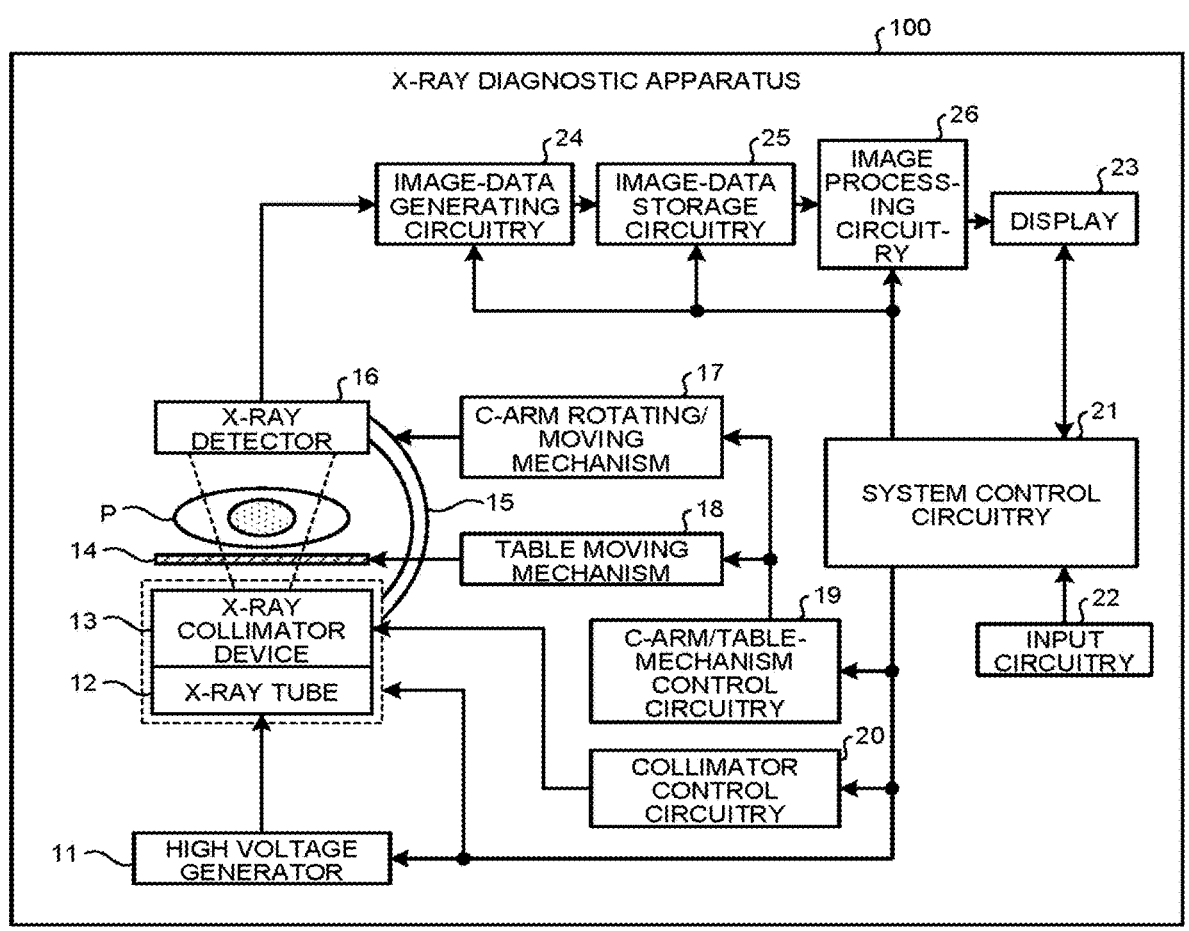
FIG. 1 depicts one example of a configuration of an X-ray diagnostic apparatus according to a first embodiment.

FIG. 1 depicts one example of a configuration of an X-ray diagnostic apparatus 100 according to a first embodiment. As shown in FIG. 1, the X-ray diagnostic apparatus 100 according to the first embodiment includes a high voltage generator 11, an X-ray tube 12, an X-ray collimator device 13, a table 14, a C-arm 15, and an X-ray detector 16. Moreover, the X-ray diagnostic apparatus 100 according to the first embodiment includes a C-arm rotating/moving mechanism 17, a table moving mechanism 18, a C-arm/table mechanism control circuitry 19, a collimator control circuitry 20, a system control circuitry 21, an input circuitry 22, and a display 23. Furthermore, the X-ray diagnostic apparatus 100 according to the first embodiment includes an image-data generating circuitry 24, an image-data storage circuitry 25, and an image processing circuitry 26.

The high voltage generator 11 generates a high voltage under a control of the system control circuitry 21, and supplies the generated high voltage to the X-ray tube 12. The X-ray tube 12 generates X-rays using the high voltage supplied by the high voltage generator 11.

The X-ray collimator device 13 narrows an X-ray generated by the X-ray tube 12 so as to be selectively irradiated to a region of interest of a subject P, under a control of the collimator control circuitry 20. For example, the X-ray collimator device 13 includes four pieces of slidable collimator blades. The X-ray collimator device 13 slides these collimator blades under a control of the collimator control circuitry 20 to narrow an X-ray that is generated by the X-ray tube 12 to be irradiated on the subject P. The table 14 is arranged on a not shown bed on which the subject P is placed. The subject P is not included in the X-ray diagnostic apparatus 100.

The X-ray detector 16 detects an X-ray that has passed through the subject P. For example, the X-ray detector 16 includes detecting elements that are aligned in a matrix.

Each of the detecting elements converts an X-ray that has passed through the subject P into an electric signal to accumulate, and transmits the accumulated electric signal to the image-data generating circuitry 24.

The C-arm 15 holds the X-ray tube 12, the X-ray collimator device 13, and the X-ray detector 16. The X-ray tube 12 and the X-ray collimator device 13, and the X-ray detector 16 are arranged, by the C-arm 15, so as to oppose to each other about the subject P.

The C-arm rotating/moving mechanism 17 is a mechanism to rotate and move the C-arm 15, and the table moving mechanism 18 is a mechanism to move the table 14. The C-arm/table mechanism control circuitry 19 controls the C-arm rotating/moving mechanism 17 and the table moving mechanism 18 under a control of the system control circuitry 21, to adjust rotation and movement of the C-arm 15, and movement of the table 14. The collimator control circuitry 20 adjusts the collimator degree of the collimator blades included in the X-ray collimator device 13 under a control of the system control circuitry 21, to control an irradiation range of X-rays that are irradiated to the subject P.

The image-data generating circuitry 24 generates image data using an electric signal converted from an X-ray by the X-ray detector 16, and stores the generated image data in the image-data storage circuitry 25. For example, the image-data generating circuitry 24 performs current/voltage conversion, analog/digital (A/D) conversion, and parallel/serial conversion on an electric signal received from the X-ray detector 16, to generate image data. For example, the image-data generating circuitry 24 generates multiple X-ray images chronologically based on X-rays that have passed through a subject into which a contrast media is injected, and that have been detected by the X-ray detector 16.

The image-data storage circuitry 25 stores image data that is generated by the image-data generating circuitry 24. For example, the image-data storage circuitry 25 stores image data obtained by chronologically imaging a predetermined region of the subject P into which a contrast media is injected.

The image processing circuitry 26 performs various kinds of image processing on the image data stored in the image-data storage circuitry 25. The image processing performed by the image processing circuitry 26 is described in detail later.

The input circuitry 22 accepts various kinds of instructions from an operator that operates the X-ray diagnostic apparatus 100, such as a doctor and a technician. For example, the input circuitry 22 includes a mouse, a keyboard, a button, a track ball, a joystick, and the like. The input circuitry 22 transfers an instruction accepted from an operator to the system control circuitry 21.

The display 23 displays a graphical user interface (GUI) to accept an instruction of an operator, image data stored in the image-data storage circuitry 25, and the like. For example, the display 23 includes a monitor. The display 23 may include more than one monitor.

The system control circuitry 21 controls overall action of the X-ray diagnostic apparatus 100. For example, the system control circuitry 21 controls a dose or ON/OFF of an X-ray irradiated to the subject P by controlling the high voltage generator 11 according to an instruction of an operator transferred from the input circuitry 22 to adjust a voltage to be supplied to the X-ray tube 12. Moreover, for example, the system control circuitry 21 controls the C-arm/table mechanism control circuitry 19 according to an instruction of an operator to adjust rotation and movement of the C-arm 15, and movement of the table 14. Furthermore, for example, the system control circuitry 21 controls the collimator control circuitry 20 according to an instruction of an operator to adjust the collimator degree of the collimator blades included in the X-ray collimator device 13, thereby controlling an irradiation range of an X-ray irradiated to the subject P.

Moreover, the system control circuitry 21 controls image-data generation processing by the image-data generating circuitry 24, image processing, analysis processing, and the like by the image processing circuitry 26 according to an instruction of an operator. Furthermore, the system control circuitry 21 controls to display the GUI to accept an instruction of an operator, an image stored in the image-data storage circuitry 25, and the like on the monitor of the display 23.

The X-ray diagnostic apparatus 100 according to the present embodiment enables to observe images of a contrast media in a blood vessel changing from a dense state to a sparse state precisely, in images of the blood vessel imaged using the contrast media. Specifically, the X-ray diagnostic apparatus 100 enables easy determination whether a residual contrast media remaining in a blood vessel is present, by processing performed by the image processing circuitry 26 explained below.

Figure 2A:
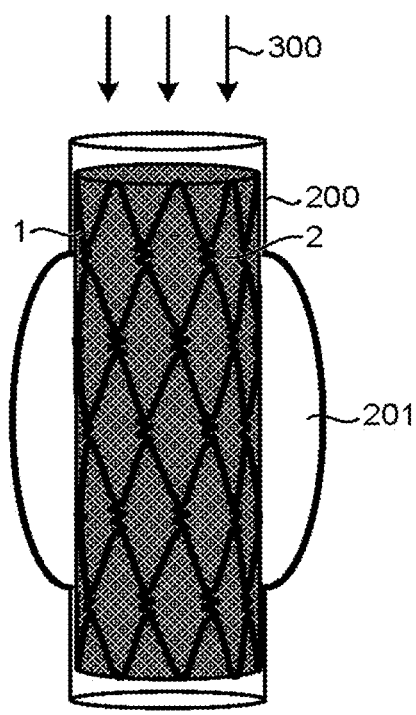
FIG. 2A is a diagram for explaining an endoleak of a stent graft according to the first embodiment.
Figure 2B:
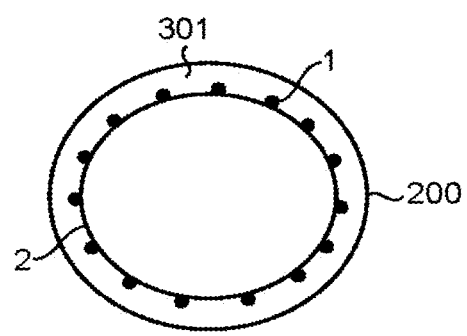
FIG. 2B is a diagram for explaining an endoleak of a stent graft according to the first embodiment.

First, as one example of observing images of a contrast media in a blood vessel changing from a dense state to a sparse state, an endoleak of a stent graft is explained using FIG. 2A and FIG. 2B. FIG. 2A and FIG. 2B are diagrams for explaining an endoleak of a stent graft according to the first embodiment. FIG. 2B is a diagram when FIG. 2A is viewed from above.

A stent graft is, for example, an artificial blood vessel 2 that is attached to an inside of a stent 1, as shown in FIG. 2A, and is used for a treatment to prevent a rupture of an aortic aneurysm 201 by attaching on an inside of the aortic aneurysm 201 formed in an aorta 200. This stent graft is, for example, put at an end of a catheter, and is inserted from an artery at a root of a leg to a position of the aortic aneurysm 201. The stent graft is then attached, by a spring of the stent and a blood pressure, to the inside of the aorta 200 at which the aortic aneurysm 201 is formed. This enables to suppress a flow of blood into the aortic aneurysm 201, thereby preventing a rupture of the aortic aneurysm 201.

When the stent graft insertion described above is performed, whether a stent graft is placed at an appropriate position, and whether an endoleak has not occurred are checked with a contrast image. When the stent graft is not attached intimately enough to the aorta 200, an endoleak in which blood flows into the aortic aneurysm 201 from a gap occurs. That is, as shown in FIG. 2B, if a gap 301 is created between the stent graft and the aorta 200 at an end of the stent graft that is constituted of the stent 1 and the artificial blood vessel 2, blood that flows in a direction of an arrow 300 in FIG. 2A flows into the gap 301, and further to the aortic aneurysm 201.

Therefore, by observing a contrast image, occurrence of an endoleak is examined. That is, if the gap 301 is formed between the stent graft and the aorta 200, a contrast media flows into the gap 301. The contrast media flowed into the gap 301 remains in the gap 301 even after the contrast media has passed through the aorta 200. An observer determines whether this residual contrast media is present, thereby examining whether a gap is present between the stent graft and the aorta 200, that is, whether an endoleak is present.

Figure 3:
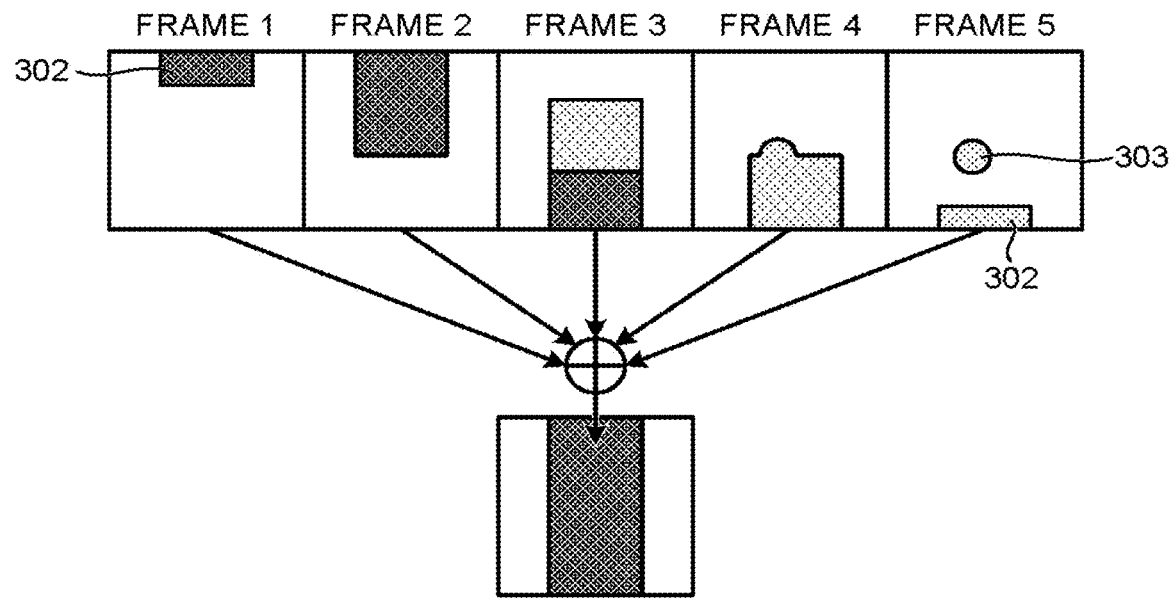
FIG. 3 is a diagram for explaining a problem in a conventional technique.

As described above, when the stent graft insertion is performed, whether an endoleak is present is examined, and it is preferable that an image in which the contrast media is emphasized be displayed therefor because an amount of the residual contrast media flowed into the gap 301 is small. However, by a conventional technique to emphasize a contrast media, it is difficult to emphasize only the residual contrast media. FIG. 3 is a diagram for explaining a problem in the conventional technique. FIG. 3 depicts a case of enhancing a contrast media using images of five frames that are imaged during the contrast media is flowing. Moreover, FIG. 3 depicts images that are imaged in order of frame 1 to frame 5. That is, the contrast media flowing in a direction from top to bottom of the drawing is depicted. Frames herein correspond to images.

For example, in the conventional technique, as shown in FIG. 3, when a contrast media is emphasized using each image showing a flow of a contrast media 302, a residual contrast media 303 is buried in the contrast media 302. That is, for example, when signal averaging processing in the conventional technique is performed, pixel values of an identical pixel in each of frame 1 to frame 5 are added, and then divided by the "number of frames: 5", thereby obtaining an image in which an entire region in which the contrast media 302 has flowed is depicted by average pixel values. Furthermore, for example, when a contrast media is emphasized by selecting the largest value from among respective values of an identical pixel in frame 1 to frame 5, an image in which an entire region in which the contrast media 302 has flowed is depicted by the largest pixel value is obtained.

Therefore, in the conventional technique, it is difficult to display an image in which only the residual contrast media 303 is emphasized, and it can be difficult to determine whether a residual contrast media is present. Accordingly, the X-ray diagnostic apparatus 100 of the present embodiment generates an image in which only a residual contrast media is emphasized by processing of the image processing circuitry 26, thereby enabling to determine whether a residual contrast media that remains in a blood vessel is present easily.

Figure 4:
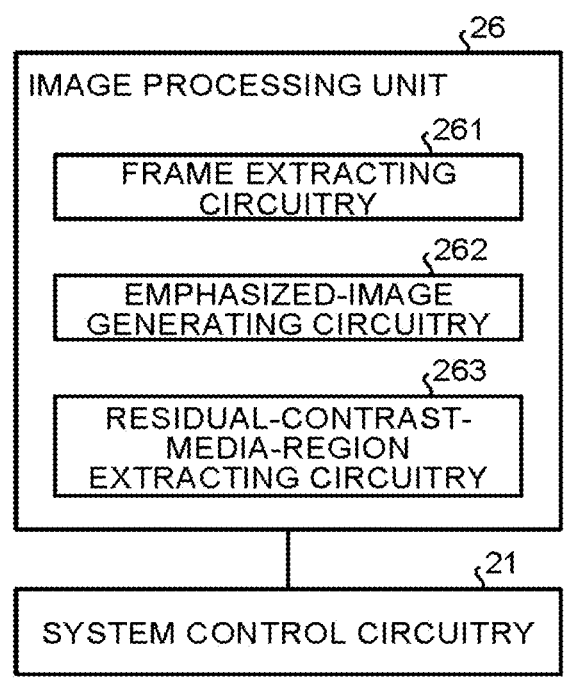
FIG. 4 depicts one example of a configuration of an image processing circuitry according to the first embodiment.

FIG. 4 depicts one example of a configuration of the image processing circuitry 26 according to the first embodiment. As shown in FIG. 4, the image processing circuitry 26 according to the first embodiment includes a frame extracting circuitry 261, an emphasized-image generating circuitry 262, and a residual-contrast media-region extracting circuitry 263, and is connected to the system control circuitry 21.

The frame extracting circuitry 261 extracts a first image that is obtained when a difference of pixel values between predetermine two images, or a predetermined region in one image becomes equal to or smaller than a threshold. Specifically, the frame extracting circuitry 261 extracts a first frame (hereinafter, described as reference frame) in which a contrast media has flowed away in a predetermined region, from among images obtained by chronologically imaging the predetermined region of a subject to which the contrast media has been given. More specifically, the frame extracting circuitry 261 reads multiple frames including frames of the contrast media shifting from a dense state to a sparse state, and a frame after the contrast media has flowed away, from the image-data storage circuitry 25, and extracts a reference frame from among the read frames.

For example, the frame extracting circuitry 261 reads all of frames corresponding to a single test imaged using a contrast media, from the image-data storage circuitry 25. The frame extracting circuitry 261 then calculates a value obtained by subtracting a pixel value of a latter frame from a pixel value of a former frame in chronologically sequential two frames.

Figure 5:
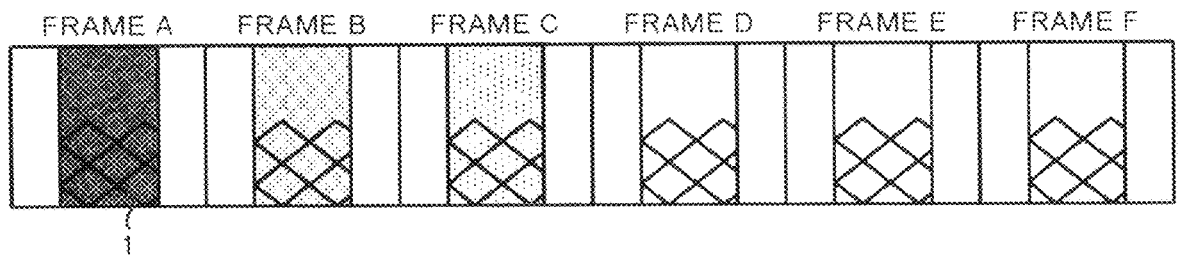
FIG. 5 is a diagram for explaining one example of processing performed by a frame extracting circuitry according to the first embodiment.

Subsequently, the frame extracting circuitry 261 performs following processing on a frame the calculated value of which is a positive value, and frames thereafter. That is, the frame extracting circuitry 261 performs the processing on multiple frames including frames of the contrast media in a dense state to a sparse state, and a frame after the contrast media has flowed away. FIG. 5 is a diagram for explaining one example of processing performed by the frame extracting circuitry 261 according to the first embodiment.

For example, the frame extracting circuitry 261 performs subtraction processing described above on respective frames from a frame A showing a dense state of a contrast media to a frame F showing a state after the contrast media has flowed away as shown in FIG. 5, and extracts a frame having a result of the processing being equal to or smaller than a predetermined threshold. As one example, the frame extracting circuitry 261 determines whether a value obtained by subtracting a pixel value of a frame B from a pixel value of the frame A is equal to or smaller than a predetermined threshold. Similarly, the frame extracting circuitry 261 subtracts a pixel value of a latter frame from a pixel value of a former frame of chronologically sequential two frames, and determines whether a value obtained by subtraction is equal to or smaller than the predetermined threshold.

When a value obtained by subtracting a pixel value of the frame F from a pixel value of a frame E is equal to or smaller than a predetermined threshold, the frame extracting circuitry 261 extracts the frame E as a reference frame. That is, the frame extracting circuitry 261 extracts a frame right after all of the contrast media including a residual contrast media has flowed away. As for the subtraction of pixel values between frames and comparison of a value with a threshold, any kind of processing can be applied, as long as subtraction is performed with pixel values of an identical pixel and then comparison with a threshold is performed. Accordingly, for example, after subtraction of pixel values is performed for all pixels, an average value of all of calculated values can be compared with a threshold, or after subtraction of pixel values is performed for pixels in a predetermined region, an average value of all of calculated values can be compared with a threshold. Alternatively, each of calculated values can be compared with a threshold, and all of the values can be determined whether it is equal to or smaller than a threshold.

The frame extracting circuitry 261 can extract a reference frame also by processing other than the processing described above. For example, the frame extracting circuitry 261 extracts a frame in which a pixel value in a predetermined region in a frame is equal to or smaller than a threshold, as a reference frame. In this case, when the largest pixel value among frames corresponding to a single test is selected for each of identical pixels of the frames, the frame extracting circuitry 261 extracts a region in which a value is equal to or larger than a threshold.

The frame extracting circuitry 261 then extracts a frame in which a pixel value in the extracted region is equal to or smaller than a threshold as a reference frame. That is, the frame extracting circuitry 261 first extracts a blood vessel region that is imaged by a contrast media in a frame, and extracts a frame in which a pixel value of the extracted blood vessel region is equal to or smaller than a threshold as a reference frame.

Referring back to FIG. 4, the emphasized-image generating circuitry 262 generates an emphasized image in which a region having a remaining contrast media is emphasized, by using the reference frame depicting a state in which the contrast media has flowed away in a predetermined region and a second frame (hereinafter, described as reverse order frame) that is followed by the reference frame in chronological sequence, out of images obtained by chronologically imaging a predetermined region of a subject to which the contrast media is injected.

Figure 6A:
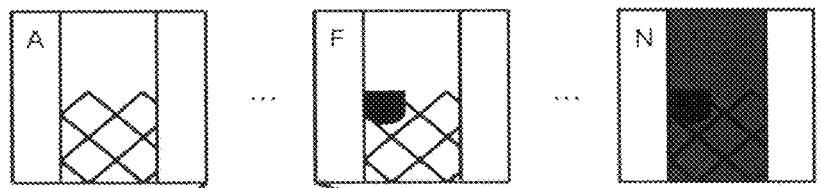
FIGS. 6A-6C are diagrams for explaining one example of processing performed by an emphasized-image generating circuitry according to the first embodiment.
Figure 6B:
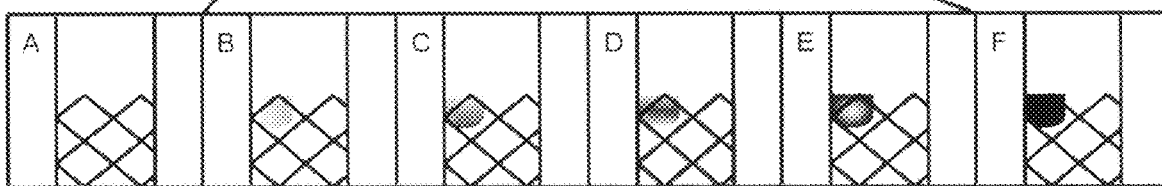
Figure 6C:
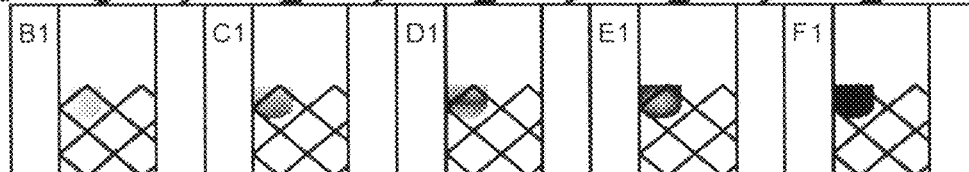

Specifically, the emphasized-image generating circuitry 262 generates an emphasized image by trace processing in which the largest pixel value of an identical pixel in the reference frame and the reverse order frame is used to depict each pixel. FIGS. 6A-6C are diagrams for explaining one example of processing performed by the emphasized-image generating circuitry 262 according to the first embodiment. FIG. 6A depicts the frame A that is the reference frame to a frame N in reverse order to chronological order in which images are taken. Moreover, although a residual contrast media of each frame is shown dark in FIGS. 6A-6C, the residual contrast media observed in each frame is shown light in an actual state.

For example, the emphasized-image generating circuitry 262 performs trace processing on each frame of the frame A, which is the reference frame, to the frame F shown in FIG. 6A. That is, the emphasized-image generating circuitry 262 first compares pixel values of identical pixels in the frame A being the reference frame and in the frame B (reverse order frame) that is imaged right before the frame A as shown in FIG. 6B and FIG. 6C, and generates an emphasized image B1 in which the largest pixel value is used as the pixel value of the concerned pixel.

Subsequently, the emphasized-image generating circuitry 262 compares pixel values of identical pixels in the generated emphasized image B1 and a frame C (reverse order frame) that is imaged right before the frame B as shown in FIG. 6B and FIG. 6C, and generates an emphasized image C1 in which the largest pixel value is used as the pixel value of the concerned pixel. As described, the emphasized-image generating circuitry 262 sequentially performs the trace processing in reverse chronological order from the reference frame. For example, the emphasized-image generating circuitry 262 performs the trace processing up to the frame F right after a mainstream of the contrast media flows as shown in FIG. 6B. Thus, the emphasized-image generating circuitry 262 can generate emphasized images that fill parts in which the contrast media is dense with each other as shown in FIG. 6C.

Generally, blood that flows into a gap between a stent graft and an artery has a stream, and therefore, the density of a contrast media also becomes nonuniform as shown in FIG. 6B. The emphasized-image generating circuitry 262 can generate emphasized images that interpolate such nonuniformity with each other by performing the trace processing.

Referring back to FIG. 4, the residual-contrast media-region extracting circuitry 263 extracts a region of a residual contrast media in the emphasized image generated by the emphasized-image generating circuitry 262. Specifically, the residual-contrast media-region extracting circuitry 263 extracts a region of a residual contrast media in the emphasized image based on the number of inflection points of a pixel value profile of the emphasized image, or on a pixel value distribution in the emphasized image.

Figure 7:
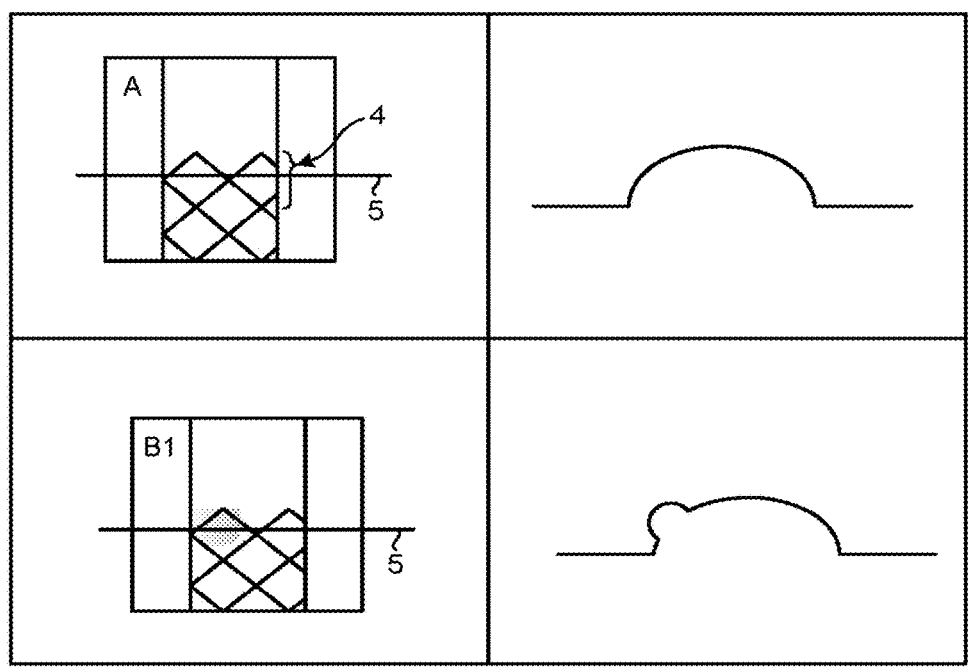
FIG. 7 is a diagram for explaining one example of processing performed by a residual-contrast media-region extracting circuitry according to the first embodiment.

FIG. 7 is a diagram for explaining one example of processing performed by the residual-contrast media-region extracting circuitry 263 according to the first embodiment. FIG. 7 depicts extraction of a contrast media region based on the number of inflection points of a profile. In FIG. 7, a frame for which profiling is performed is shown on a left side, and a profiling example of the frame is shown on a right side. For example, when a contrast media region is extracted based on the number of inflection points of a profile, the residual-contrast media-region extracting circuitry 263 determines a position at which profiling is performed first.

As one example, the residual-contrast media-region extracting circuitry 263 extracts a reference frame, or an end portion (arrow 4) of a stent graft on a side from which blood flows in after a contrast media has flowed away, as shown in an upper left drawing in FIG. 7. Subsequently, the residual-contrast media-region extracting circuitry 263 performs profiling at a line 5 that passes the extracted end portion in a direction perpendicular to a direction of a blood vessel as shown in the upper left drawing in FIG. 7. At this time, the residual-contrast media-region extracting circuitry 263 removes inflection points of the profile originated in a stent. The residual-contrast media-region extracting circuitry 263 then counts the number of inflection points, and determines that a residual contrast media region is present when there is more than one inflection point. For example, the residual-contrast media-region extracting circuitry 263 determines that no residual contrast media region is included because the number of inflection point is one in an upper right drawing in FIG. 7.

The residual-contrast media-region extracting circuitry 263 extracts a residual contrast media region by performing the profiling described above sequentially on the emphasized images generated by the emphasized-image generating circuitry 262. For example, after acquiring a profile of the frame A, which is the reference frame, the residual-contrast media-region extracting circuitry 263 acquires a profile of the line 5 in the emphasized image B1 as shown in a lower left drawing in FIG. 7. Because there are two inflection points of the profile as shown in a lower right drawing in FIG. 7, the residual-contrast media-region extracting circuitry 263 determines that a residual contrast media region is included therein, and extracts the residual contrast media region from the position of the profile.

The profiling described above may be performed once for a region of the end portion (arrow 4) of the stent, or may be performed at more than one line for the region of the end portion (arrow 4) of the stent, shifting positions gradually.

Furthermore, the residual-contrast media-region extracting circuitry 263 can extract a residual contrast media region by analyzing a pixel value distribution of each emphasized image generated by the emphasized-image generating circuitry 262. Specifically, when there is a region in a predetermined size having pixel values higher than pixel values therearound in each frame, the residual-contrast media-region extracting circuitry 263 extracts the region as a residual contrast media region.

Referring back to FIG. 4, the system control circuitry 21 controls to display emphasized images that are generated by the emphasized-image generating circuitry 262 sequentially after the reference frame on the display 23. Specifically, the system control circuitry 21 controls to display the emphasized images that are generated by the emphasized-image generating circuitry 262 in generated order on the display 23 with the reference frame as a starting image. In other words, the system control circuitry 21 controls to display the emphasized images from the reference frame in reverse chronological order that is reverse to chronological order in which images are taken. That is, after the reference frame is extracted, the display 23 displays frames that are generated prior to the reference frame in reverse chronological order.

Figure 8:
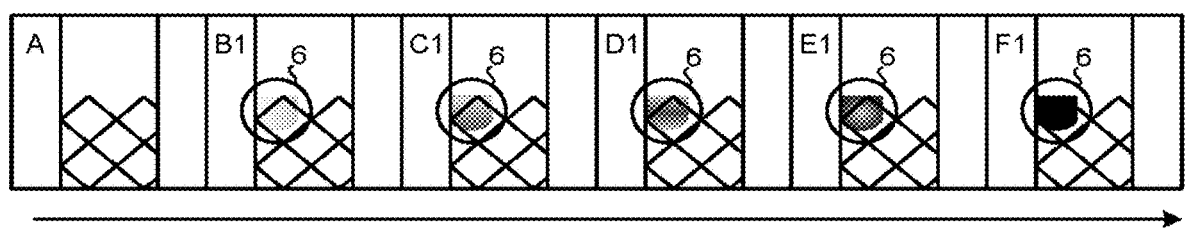
FIG. 8 is a diagram for explaining one example of processing performed by a system control circuitry according to the first embodiment.

FIG. 8 is a diagram for explaining one example of processing performed by the system control circuitry 21 according to the first embodiment. FIG. 8 depicts reverse chronological reproduction of the emphasized images generated by the trace processing shown in FIGS. 6A-6C. For example, the system control circuitry 21 controls to display frames on the display 23 starting from the reference frame, and followed by the frame B1 to a frame F1 sequentially as indicated by an arrow in FIG. 8. That is, the system control circuitry 21 reproduces the frame B1 to the frame FIG. 1 in which the residual contrast media is emphasized by the trace processing in reverse chronological order on the display 23. In other words, the system control circuitry 21 reproduces a moving image from the frame A to the frame F. Thus, the X-ray diagnostic apparatus 100 can display a moving image in which a residual contrast media gradually becomes dense, and enables an observer to determine whether a residual contrast media is present easily.

The display method of the frame A to the frame FIG. 1 is not limited to display with a moving image described above, and for example, a display method in which a displayed frame is changed every predetermined time may also be applied. In such a case also, the X-ray diagnostic apparatus 100 can display images in which a region of a residual contrast media gradually becomes dense, and enables an observer to determine whether a residual contrast media is present easily.

When a residual contrast media region is extracted by the residual-contrast media-region extracting circuitry 263, the system control circuitry 21 performs warning display, for example, by circling the residual contrast media region with a circle 6 as shown in FIG. 8. That is, the display 23 displays a mark indicating a region in which a contrast media remains in an emphasized image. Thus, the X-ray diagnostic apparatus 100 can show whether a residual contrast media is present clearly, and enables an observer to determine whether a residual contrast media is present easily. The warning display shown in FIG. 8 is only one example, and the embodiment is not limited thereto. For example, the system control circuitry 21 may surround a residual contrast media region with a shape other than a circle, may change the color of an image, or may display a text.

Determination of a reference frame, determination of a subject region when extracting a reference frame, the number of reverse order frames to generate emphasized images, and the like described in the first embodiment can be arbitrarily set and operated by an observer through the input circuitry 22. That is, in the X-ray diagnostic apparatus 100 according to the first embodiment, multiple frames that are generated prior to a reference frame can be displayed in reverse chronological order, based on an operation made through the input circuitry 22.

Figure 9:
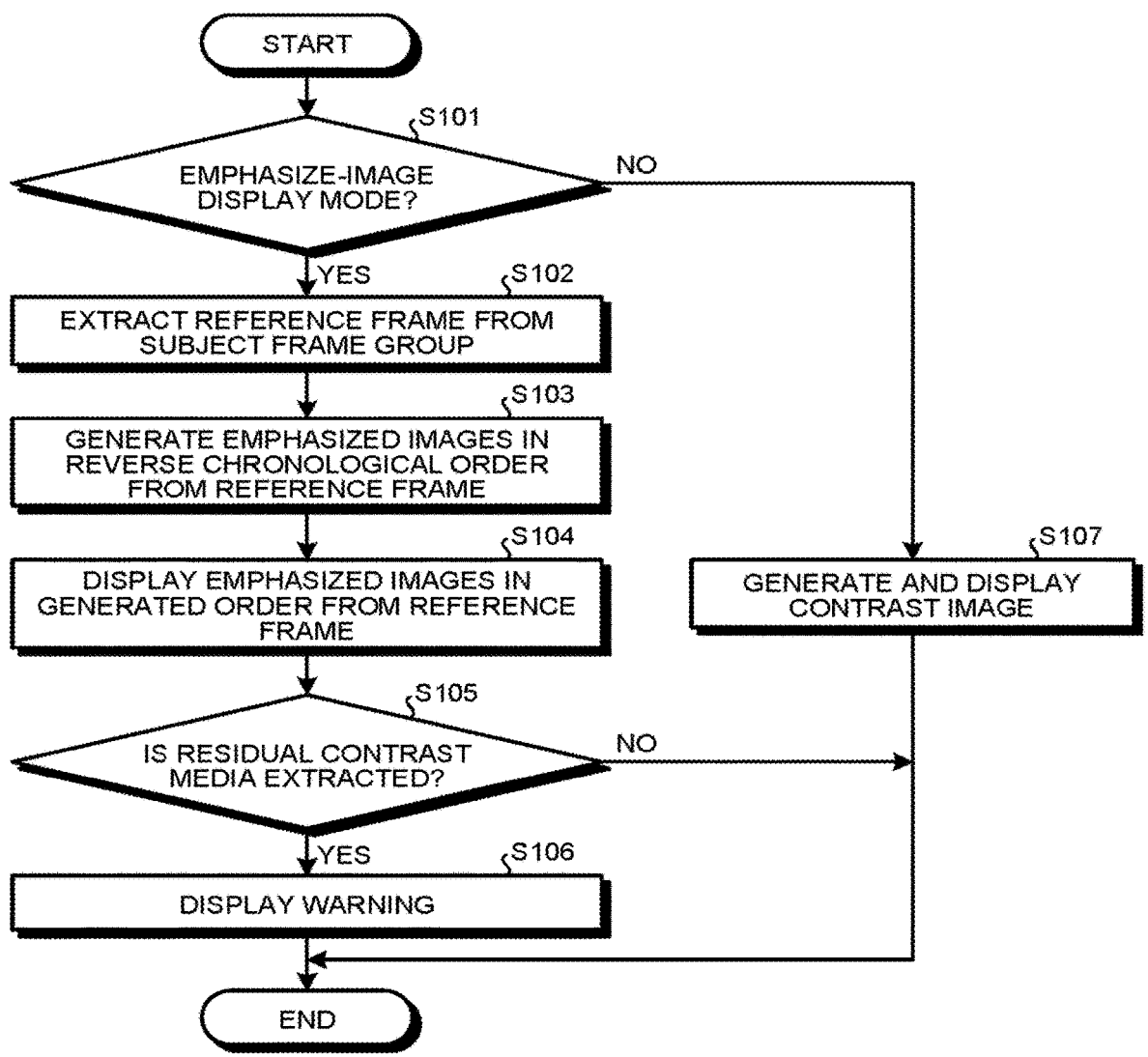
FIG. 9 is a flowchart indicating a procedure of processing performed by the X-ray diagnostic apparatus according to the first embodiment.

Next, processing of the X-ray diagnostic apparatus 100 according to the first embodiment is explained using FIG. 9. FIG. 9 is a flowchart indicating a procedure of processing performed by the X-ray diagnostic apparatus 100 according to the first embodiment. As shown in FIG. 9, in the X-ray diagnostic apparatus 100 according to the first embodiment, when it is in an emphasized-image display mode (step S101: YES), the frame extracting circuitry 261 extracts a reference frame from a subject frame group (step S102).

The emphasized-image generating circuitry 262 then generates emphasized images in reverse order to chronological order at the time of imaging from the extracted reference frame (step S103). Subsequently, the system control circuitry 21 controls to display the emphasized images on the display 23 in generated order (reverse chronological order) by the emphasized-image generating circuitry 262, following the reference frame (step S104).

The residual-contrast media-region extracting circuitry 263 performs processing of extracting a residual contrast media each time an emphasized image is generated by the emphasized-image generating circuitry 262. The system control circuitry 21 determines whether a residual contrast media is extracted by the residual-contrast media-region extracting circuitry 263 (step S105).

When a residual contrast media is extracted (step S105: YES), the system control circuitry 21 displays a warning (step S106), and ends the processing. On the other hand, when a residual contrast media is not extracted (step S105: NO), the system control circuitry 21 ends the processing. When it is not in the emphasized-image display mode (step S101: NO), the X-ray diagnostic apparatus 100 generates and displays a contrast image (step S107), and ends the processing.

As described above, according to the first embodiment, the emphasized-image generating circuitry 262 generates an emphasized image in which a region in which a contrast media remains is emphasized, using a reference frame in which the contrast media has flowed away in a predetermined region, and a reverse frame that is followed by the reference frame in chronological order among multiple frames obtained by chronologically imaging a predetermined region of a subject to which the contrast media is injected. The system control circuitry 21 controls to display the emphasized images sequentially, following the reference frame on the display 23. Therefore, the X-ray diagnostic apparatus 100 according to the first embodiment can display images in which a residual contrast media becomes dense, and enables easy determination whether a residual contrast media is present.

Furthermore, according to the first embodiment, the emphasized-image generating circuitry 262 generates multiple emphasized images using, in reverse chronological order, multiple reverse order frames. The system control circuitry 21 controls to display the emphasized images generated by the emphasized-image generating circuitry 262 in reverse chronological order following the reference frame on the display 23. Therefore, the X-ray diagnostic apparatus 100 according to the first embodiment can display a moving image that depicts a residual contrast media gradually becoming dense, and the like, and enables to determine whether a contrast media remains more accurately.

Moreover, according to the first embodiment, the emphasized-image generating circuitry 262 generates an emphasized image by performing the trace processing in which the largest pixel value among identical pixels in a reference frame and reverse order frames is used for each pixel included in an emphasized image. Therefore, the X-ray diagnostic apparatus 100 according to the first embodiment enables to display an image in which only a region of a residual contrast media is depicted gradually dense.

Furthermore, according to the first embodiment, the frame extracting circuitry 261 extracts a reference frame from multiple frames that are obtained by chronologically imaging a predetermined region of a subject to which a contrast media is injected. Therefore, the X-ray diagnostic apparatus 100 according to the first embodiment enables to extract a reference frame automatically.

Moreover, according to the first embodiment, the frame extracting circuitry 261 extracts, from among multiple frames that are obtained by chronologically imaging a predetermined region of a subject to which a contrast media is injected, a chronologically former frame out of chronologically sequential frames in which a difference in a pixel value between the frames is equal to or smaller than a predetermined threshold, as a reference frame. Therefore, the X-ray diagnostic apparatus 100 according to the first embodiment can extract a reference frame based on a pixel value of a subject frame, and enables to extract an image in which a contrast media has flowed away at high accuracy.

Furthermore, according to the first embodiment, the frame extracting circuitry 261 extracts a frame in which a pixel value of a predetermined region is equal to or smaller than a predetermined threshold as a reference frame, from among multiple frames that are obtained by chronologically imaging a predetermined region of a subject to which a contrast media is injected. Therefore, the X-ray diagnostic apparatus 100 according to the first embodiment enables to use a desirable region as a subject of determination in extracting a reference frame.

Moreover, according to the first embodiment, the frame extracting circuitry 261 determines a region in which a pixel value is equal to or larger than a predetermined threshold as a predetermined region in multiple frames. Therefore, the X-ray diagnostic apparatus 100 according to the first embodiment can specify only a region in which a contrast media flows as a subject of determination in extracting a reference frame, and enables to improve the accuracy in extraction.

Furthermore, according to the first embodiment, the residual-contrast media-region extracting circuitry 263 extracts a region in which a contrast media remains, based on analysis of a pixel value distribution in an emphasized image that is generated by the emphasized-image generating circuitry 262, or the number of inflection points in a profile of an emphasized image. Therefore, X-ray diagnostic apparatus 100 according to the first embodiment enables to extract a region of a residual contrast media automatically.

Moreover, according to the first embodiment, the residual-contrast media-region extracting circuitry 263 extracts an end portion of a stent included in a frame, and performs profiling of a proximity to the extracted end portion of the stent. Therefore, X-ray diagnostic apparatus 100 according to the first embodiment enables to extract an endoleak of a stent graft.

Second Embodiment

In the first embodiment described above, a case in which an emphasized image is generated by the trace processing has been explained. In a second embodiment, a case in which an emphasized image is generated by signal averaging processing is explained. That is, in the second embodiment, processing performed by the emphasized-image generating circuitry 262 shown in FIG. 4 is different. In the following, this is mainly explained.

Figure 10:
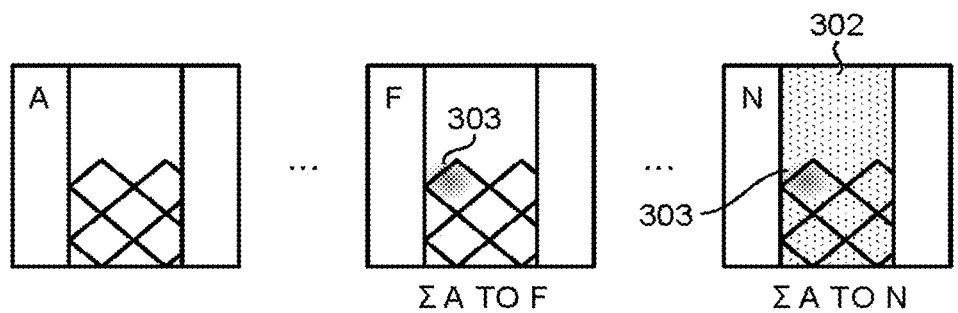
FIG. 10 is a diagram for explaining one example of processing performed by an emphasized-image generating circuitry according to a second embodiment.

The emphasized-image generating circuitry 262 according to the second embodiment performs signal averaging processing in which pixel values of an identical pixel in a reference frame and reverse order frames are added and then divided by the number of pieces of images added, thereby generating the emphasized image described above. FIG. 10 is a diagram for explaining one example of processing performed by the emphasized-image generating circuitry 262 according to the second embodiment. FIG. 10 depicts a case in which the signal averaging processing is performed on the frame A to the frame N shown in FIG. 6A.

For example, the emphasized-image generating circuitry 262 generates an emphasized image that is obtained by adding pixel values of an identical pixel in six pieces of frames from the frame A to the frame F and then dividing by the number of frames "6" as shown in FIG. 10. The emphasized-image generating circuitry 262 generates emphasize images by performing the signal averaging processing sequentially to the frame N as shown in FIG. 10. That is, the emphasized-image generating circuitry 262 performs the signal averaging each time one piece of frame is added in reverse chronological order from the reference frame, to generate an emphasized image each time. Thus, the emphasized-image generating circuitry 262 can generate an emphasized image in which contrast to the background is further emphasized.

The system control circuitry 21 controls to display the emphasized images that are generated by the signal averaging processing performed by the emphasized-image generating circuitry 262 in generated order following the reference frame as a starting image on the display 23. That is, the system control circuitry 21 reproduces the emphasized images in reverse chronological order that is reverse order to chronological order in which the respective frames are generated. Also in the system control circuitry 21 according to the second embodiment, the emphasized images can be displayed as a moving image, or can be displayed by changing frames every predetermined time, similarly to the first embodiment.

As described above, according to the second embodiment, the emphasized-image generating circuitry 262 generates an emphasized image by performing signal averaging processing in which pixel values of an identical pixel in a reference frame and reverse order frames are added and then divided by the number of frames. Therefore, the X-ray diagnostic apparatus 100 according to the second embodiment can display images in which contrast to the background is further emphasized such that a contrast media gradually becomes dense, and enables to determine whether a residual contrast media is present easily.

Third Embodiment

In the second embodiment described above, a case in which an emphasized image is generated by signal averaging processing has been explained. In a third embodiment, a case in which an emphasized image is generated by weighting in the signal averaging processing is explained. That is, in the third embodiment, processing performed by the emphasized-image generating circuitry 262 shown in FIG. 4 is different. In the following, this is mainly explained.

Figure 11:
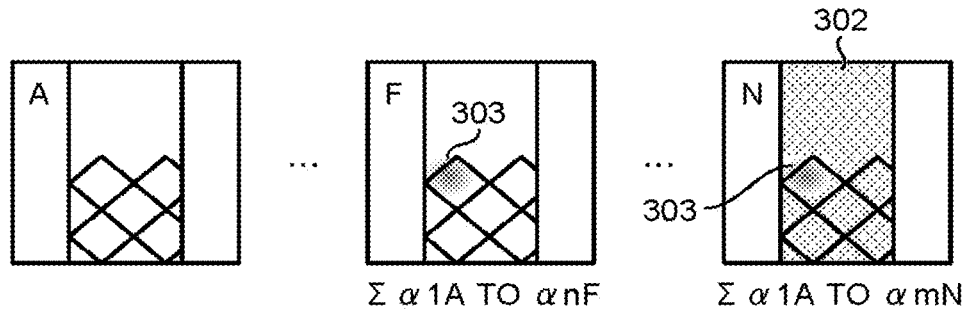
FIG. 11 is a diagram for explaining one example of processing performed by an emphasized-image generating circuitry according to a third embodiment.

The emphasized-image generating circuitry 262 according to the third embodiment gives a largest weight to a reference frame, and gives gradually decreased weights to reverse order frames when signal averaging processing is performed. FIG. 11 is a diagram for explaining one example of processing performed by the emphasized-image generating circuitry 262 according to the third embodiment. FIG. 11 depicts a case in which weighted signal-averaging processing is performed on the frame A to the frame N shown in FIG. 6A.

For example, as shown in FIG. 11, when signal averaging pixel values of an identical pixel in six pieces of frames from the frame A to the frame F, the emphasized-image generating circuitry 262 multiplies the respective pixel values by coefficients $\alpha 1$ to $\alpha n$. The coefficients $\alpha 1$ to $\alpha n$ are set to take gradually smaller values from $\alpha 1$ as the largest value. Thus, it is possible to multiply a frame having a high possibility of presence of a contrast media other than a residual contrast media in a background by a small coefficient, and even if a contrast media is present in a background, contrast can be emphasized.

The emphasized-image generating circuitry 262 then generates an emphasized image by performing weighted signal-averaging processing sequentially to the frame N as shown in FIG. 11. That is, the emphasized-image generating circuitry 262 performs the signal averaging processing weighted with coefficients gradually becoming smaller, each time one piece of frame is added in reverse chronological order from the reference frame, to generate an emphasized image each time. Thus, the emphasized-image generating circuitry 262 can generate an emphasized image in which contrast is further emphasized to the background.

The system control circuitry 21 controls to display the emphasized images that are generated by the weighted signal-averaging processing performed by the emphasized-image generating circuitry 262 in generated order following the reference frame as a starting image on the display 23. That is, the system control circuitry 21 reproduces the emphasized images generated by the signal averaging processing in reverse chronological order that is reverse order to chronological order in which the respective frames are generated. Also in the system control circuitry 21 according to the second embodiment, the emphasized images can be displayed as a moving image, or can be displayed by changing frames every predetermined time, similarly to the first embodiment.

As described above, according to the third embodiment, the emphasized-image generating circuitry 262 assigns the largest weight to a reference frame and assigns weights that gradually becomes small to reverse order frames, when the signal averaging processing is performed. Therefore, the X-ray diagnostic apparatus 100 according to the third embodiment can display images in which contrast to the background is further emphasized such that a contrast media gradually becomes dense, and enables to determine whether a residual contrast media is present easily.

Fourth Embodiment

The first embodiment has been explained; however, various other embodiments may be applied other than the first embodiment.

In the first to the third embodiments, a case in which an endoleak of a stent graft is observed as an example of observing a residual contrast media has been explained. However, embodiments are not limited thereto, and it is applicable to any examination as long as the examination is to observe a residual contrast media.

In the first to the third embodiments, a case in which a value obtained by subtracting a pixel value of a latter frame from a pixel value of a former frame in two chronologically sequential frames is compared with a threshold, and a frame having a value equal to or smaller than a predetermined threshold is extracted as a reference frame has been explained. However, embodiments are not limited thereto, and for example, an identical comparison resource frame may be compared with another frame.

In such a case, for example, the frame extracting circuitry 261 reads multiple frames that include frames of the contrast media in a dense state to a sparse state, and a frame after the contrast media has flowed away. The frame extracting circuitry 261 uses the final frame in chronological order among the read frames as a comparison resource frame, and determines whether a value obtained by subtracting a pixel value of the comparison resource frame from a pixel value of the first frame in the chronological order is equal to or smaller than a predetermined threshold. Similarly, the frame extracting circuitry 261 determines whether a value obtained by subtracting a pixel value of the comparison resource frame from a pixel value of a frame that follows the first frame in the chronological order is equal to or smaller than the predetermined threshold. Thus, the frame extracting circuitry 261 compares each of the frames with the comparison resource frame in chronological order, and extracts a frame having a subtracted value that is equal to or smaller than the predetermined threshold as a reference frame. Although a case in which a final frame in chronological order is used as a comparison resource frame among read multiple frames has been explained in the above example, embodiments are not limited thereto, and an arbitrary frame can be used as a comparison resource frame as long as the frame is one corresponding to a moment after a contrast media has flowed away.

Moreover, extraction of a reference frame is not limited to the extraction based on a change in pixel values between two images described above, and a reference frame may be extracted using a pixel value of a region in a single image. In such a case, for example, the frame extracting circuitry 261 reads multiple frames that includes frames of the contrast media shifting from a dense state to a sparse state, and a frame after the contrast media has flowed away. The frame extracting circuitry 261 then determines whether a pixel value of a predetermined region in the first frame in chronological order is equal to or smaller than a predetermined threshold. Similarly, the frame extracting circuitry 261 determines whether a pixel value of the predetermined region in a frame that follows the first frame in the chronological order is equal to or smaller than a predetermined threshold. Thus, the frame extracting circuitry 261 compares a pixel value of a predetermined region of each of frames with a predetermined threshold in chronological order, and extracts a frame having a value equal to or smaller than the threshold as a reference frame. The predetermined region in a frame described above may be determined by extracting a region including a blood vessel by the frame extracting circuitry 261, or may be determined arbitrarily by an operator.

A case in which the X-ray diagnostic apparatus generates an emphasized image has been explained in the first to the third embodiments. The processing described above may be performed by an image processing apparatus such as a workstation. In such a case, for example, a workstation that is connected to an X-ray diagnostic apparatus, an image storage device, and the like through a network acquires image data from the X-ray diagnostic apparatus, the image storage device, and the like. The workstation then performs the processing described above using the acquired image data.

As explained above, according to the first to the fourth embodiments, the X-ray diagnostic apparatus and the image processing apparatus of the embodiments enables to determine whether a residual contrast media is present easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray diagnostic apparatus comprising:
an X-ray generator configured to irradiate a plurality of X-rays to a subject;

an X-ray detector configured to detect the plurality of X-rays;

processing circuitry configured to
generate a first plurality of X-ray images chronologically based on the plurality of X-rays that have passed through the subject into which a contrast media is injected, and that have been detected by the X-ray detector, calculate, for the first plurality of X-ray images, a differential value obtained by subtracting a pixel value in a region of a latter image from a pixel value in a region of a former image in chronologically sequential two images, respectively, extract, from the first plurality of X-ray images, a second plurality of X-ray images subsequent to the latter image for which the calculated differential value is a positive value, extract a first image from among the second plurality of X-ray images, the first image being a former image in which the calculated differential value is equal to or smaller than a threshold, and sequentially generate a plurality of emphasized images by sequentially performing trace processing or signal averaging processing on two or more X-ray images from the latter image for which the calculated differential value is the positive value to the first image in reverse chronological order; and a display configured to display the plurality of emphasized images in order in which the plurality of emphasized images were generated.

2. The X-ray diagnostic apparatus according to claim 1, wherein the processing circuitry is further configured to be operated by an operator, wherein
the display is configured to display the plurality of emphasized images based on operation by the operator.

3. The X-ray diagnostic apparatus according to claim 1, wherein the display is configured to display the plurality of emphasized images as a moving image.

4. The X-ray diagnostic apparatus according to claim 1, wherein the trace processing is processing for extracting a largest pixel value for each pixel in the two or more X-ray images, and the signal averaging processing is processing for signal averaging the two or more X-ray images.

5. The X-ray diagnostic apparatus according to claim 1, wherein the processing circuitry is further configured to extract a region in which the contrast media remains, based on analysis of a pixel value distribution in an emphasized image of the plurality of emphasized images, or number of inflection points in a profile of the emphasized image.

6. The X-ray diagnostic apparatus according to claim 5, wherein the processing circuitry is configured to extract the region in which the contrast media remains by calculating a profile of a stent end region in the emphasized image.

7. The X-ray diagnostic apparatus according to claim 5, wherein the display is configured to display, in the emphasized image, a mark that indicates the region in which the contrast media remains.

8. An image processing apparatus comprising:
processing circuitry configured to
generate a first plurality of X-ray images chronologically based on X-rays that have passed through a subject into which a contrast media is injected, calculate, for the first plurality of X-ray images, a differential value obtained by subtracting a pixel value in a region of a latter image from a pixel value in a region of a former image in chronologically sequential two images, respectively, extract, from the first plurality of X-ray images, a second plurality of X-ray images subsequent to the latter image for which the calculated differential value is a positive value, extract a first image from among the second plurality of X-ray images, the first image being a former image in which the calculated differential value is equal to or smaller than a threshold, and sequentially generate a plurality of emphasized images by sequentially performing trace processing or signal averaging processing on two or more X-ray images from the latter image for which the calculated differential value is the positive value to the first image in reverse chronological order; and a display configured to display the plurality of emphasized images in order in which the plurality of emphasized images were generated.

9. An image processing method comprising:
generating a first plurality of X-ray images chronologically based on X-rays that have passed through a subject into which a contrast media is injected;

calculating, for the first plurality of X-ray images, a differential value obtained by subtracting a pixel value in a region of a latter image from a pixel value in a region of a former image in chronologically sequential two images, respectively;

extracting, from the first plurality of X-ray images, a second plurality of X-ray images subsequent to the latter image for which the calculated differential value is a positive value;

extracting a first image from among the second plurality of X-ray images, the first image being a former image in which the calculated differential value is equal to or smaller than a threshold;

sequentially generating a plurality of emphasized images by sequentially performing trace processing or signal averaging processing on two or more X-ray images from the latter image for which the calculated differential value is the positive value to the first image in reverse chronological order; and displaying the plurality of emphasized images in order in which the plurality of emphasized images were generated.

* * * * *